United States Patent
Spohn et al.

(10) Patent No.: US 10,522,250 B2
(45) Date of Patent: Dec. 31, 2019

(54) SYSTEMS FOR DETERMINING, AND DEVICES FOR INDICATING, VIABLE LIFE OF REPLACEABLE COMPONENTS THEREOF AND METHODS THEREFOR

(71) Applicant: BAYER HEALTHCARE LLC, Whippany, NJ (US)

(72) Inventors: Michael Spohn, Fenelton, PA (US); Michael Swantner, Saxonburg, PA (US); Edward Rhinehart, Monroeville, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 9 days.

(21) Appl. No.: 15/750,878

(22) PCT Filed: Aug. 11, 2016

(86) PCT No.: PCT/US2016/046587
§ 371 (c)(1),
(2) Date: Feb. 7, 2018

(87) PCT Pub. No.: WO2017/027724
PCT Pub. Date: Feb. 16, 2017

(65) Prior Publication Data
US 2018/0240548 A1 Aug. 23, 2018

Related U.S. Application Data

(60) Provisional application No. 62/204,879, filed on Aug. 13, 2015.

(51) Int. Cl.
*G16H 40/40* (2018.01)
*A61M 5/142* (2006.01)
(Continued)

(52) U.S. Cl.
CPC ............ *G16H 40/40* (2018.01); *A61M 5/142* (2013.01); *A61M 5/1723* (2013.01);
(Continued)

(58) Field of Classification Search
CPC .............. A61M 5/16854; A61M 5/142; A61M 5/1723; A61M 5/172; F24F 11/39;
(Continued)

(56) References Cited

U.S. PATENT DOCUMENTS

| 3,977,391 A | 8/1976 | Fleischmann |
| 7,775,966 B2 | 8/2010 | Dlugos et al. |

(Continued)

FOREIGN PATENT DOCUMENTS

WO  2015106107 A1  7/2015

OTHER PUBLICATIONS

"International Preliminary Report on Patentability from PCT Application No. PCT/US2016/046587", dated Feb. 22, 2018.
(Continued)

*Primary Examiner* — Eric Blount
(74) *Attorney, Agent, or Firm* — James R. Stevenson; Neil Friedrich

(57) ABSTRACT

A system capable of monitoring a replaceable component is provided. The system includes a controller for controlling operation of the system; programming instructions according to which the system is configured to: accept input of a viable life for the component, calculate an accumulated amount of distress experienced by the component based on each set of previously collected use data associated with each previous use of the component, and determine, based in part on the accumulated amount of distress, a used portion of the viable life that the component has experienced as a result of the previous use(s) thereof and an unused portion of the viable life; and a feedback device configured to
(Continued)

provide to an operator of the system an indication of at least one of the unused and used portions of the viable life of the component. Methods of monitoring a replaceable component of a system are also provided.

24 Claims, 13 Drawing Sheets

(51) Int. Cl.
*G06F 19/00* (2018.01)
*G16H 40/63* (2018.01)
*A61M 5/172* (2006.01)
*G06Q 10/00* (2012.01)
*G16H 20/17* (2018.01)

(52) U.S. Cl.
CPC ......... *G06F 19/3468* (2013.01); *G16H 40/63* (2018.01); *A61M 2005/14268* (2013.01); *A61M 2005/1726* (2013.01); *A61M 2205/18* (2013.01); *A61M 2205/332* (2013.01); *A61M 2205/3331* (2013.01); *A61M 2205/3368* (2013.01); *A61M 2205/50* (2013.01); *A61M 2205/502* (2013.01); *A61M 2205/581* (2013.01); *A61M 2205/583* (2013.01); *A61M 2205/702* (2013.01); *G06Q 10/20* (2013.01); *G16H 20/17* (2018.01)

(58) Field of Classification Search
CPC ........ G16H 30/40; G16H 40/63; G16H 40/40; G06F 19/3468
USPC ....................................................... 340/679
See application file for complete search history.

(56) References Cited

U.S. PATENT DOCUMENTS

| | | | |
|---|---|---|---|
| 8,095,241 B2 | 1/2012 | Palmerton et al. | |
| 2002/0070157 A1 | 6/2002 | Yamada | |
| 2010/0305506 A1 | 12/2010 | Fahrer et al. | |
| 2016/0045841 A1* | 2/2016 | Kaplan | B01J 19/0093 429/49 |

OTHER PUBLICATIONS

"International Search Report and Written Opinion from PCT Application No. PCT/US2016/046587", dated Oct. 26, 2016.
"Supplementary Partial European Search Report from EP Application No. EP16835924", dated Feb. 14, 2019.

* cited by examiner

SYSTEMS FOR DETERMINING, AND DEVICES FOR INDICATING, VIABLE LIFE OF REPLACEABLE COMPONENTS THEREOF AND METHODS THEREFOR

CROSS-REFERENCE TO RELATED APPLICATIONS

This application is a 371 national phase application of PCT International Application No. PCT/US2016/046587, filed Aug. 11, 2016, which is based on and claims priority to U.S. Provisional Application No. 62/204,879, filed Aug. 13, 2015, each of which is incorporated herein by reference in its entirety.

BACKGROUND

Field

This disclosure relates to fluid injectors and fluid delivery systems and, in particular, to systems and methods for monitoring or tracking the remaining or unused viable life of replaceable injector components during fluid injection procedures.

Description of Related Art

Some diagnostic and therapeutic procedures involve injecting a fluid, such as a therapeutic agent, contrast agent, or nutrient solution to a patient. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these medical fluid delivery systems are designed to deliver a preset amount of fluid at a preset flow rate.

In some injection procedures, a medical practitioner places a catheter or needle into a vein or artery of the patient. The catheter or needle is connected to a manual or an automatic fluid injector system by way of tubing and a connector that interfaces with the fluid injector system. Automatic fluid injector systems typically include at least one syringe connected to at least one fluid injector having, for example, a powered linear piston. The at least one syringe includes, for example, a source of contrast and/or a source of flushing fluid The medical practitioner enters settings (referred to herein as "injection parameter settings") into an electronic control system of the fluid injector for a fixed volume of contrast and/or saline and a fixed rate of injection.

The injector device can include a Multi-Use Disposable fluid path Set ("MUDS") with tubing and connectors for transporting fluid from the syringe to an outflow port of the injector. The MUDS tubing and connectors are generally formed from flexible plastic materials that deform or degrade with repeated use. The MUDS can be connected to a single-use disposable set (SUDS) for transporting fluid from the MUDS to the patient.

System operators must monitor and document use of the MUDS to determine when it needs to be removed and replaced. For example, a reusable component such as the MUDS may need to be replaced every 12, 24, or 48 hours. Alternatively, the MUDS may be scheduled to be replaced following a specified number of injection procedures. However, determining when the MUDS or other components should be replaced can be difficult since the injector can be used by different operators or during multiple shifts during the lifespan of the MUDS or other components. Currently, operators monitor MUDS lifespan by recording when a MUDS is installed and a number of uses on a tag or label attached to the injector or MUDS. For example, the injector operator might write the date and time for each use in an appropriate line on the label or tag. Once all available spaces for writing the date and time are filled in, the MUDS should be removed and replaced. However, such manual recording methods require injector operators to diligently check and update the label or tag prior to and following each injection activity.

In order to ensure proper function and performance throughout the lifecycle of the replaceable component, the components, such as the MUDS, are typically manufactured to withstand the maximum pressure and flow volumes that they would likely experience throughout their respective lifecycles. Accordingly, replaceable components are manufactured with pressure tolerances far beyond actual levels applied during a conventional injection procedure. The SUDS is also manufactured to withstand forces in excess of the maximum pressure and flow rate that it would encounter during normal usage. However, since the SUDS is only used by a single patient and then discarded, the risk of rupture or failure is reduced.

While various manual and automatic fluid delivery systems are known in the medical field, improved fluid delivery systems adapted for use in medical diagnostic and therapeutic procedures are desirable. In particular, injector systems with self-monitoring functions that are capable of monitoring the status of replaceable injector components, such as the MUDS, and of providing a visual indication or representation of lifecycle for the replaceable injector components are needed. Providing a visual indication of lifecycle would help to prevent distress to the injector from worn out, replaceable components by providing a more accurate and sophisticated indication of when such replaceable components should be removed and replaced.

SUMMARY

In view of the foregoing, a need exists for a fluid delivery system including an injector associated with a controller, computing unit, or remote computer device that tracks the lifecycle of disposable and/or replaceable injector components, such as the MUDS, and provides appropriate feedback to a system operator regarding the same. The system should be capable of monitoring or tracking remaining viable life for the replaceable injector components based on calculated accumulated or estimated amount of distress that the replaceable component is subjected to as a result of actual (or planned) injection procedures. The calculated accumulated or estimated amounts of distress can be determined based on a combination of experimental data about the replaceable components, data provided from sensors positioned throughout the injector that are configured to measure injection forces and/or distress to the replaceable injector components, and injection parameter settings and related information from the electronic control system of the fluid delivery system.

The fluid delivery system can also be integrated with other injector control systems to prevent the injector from performing an injection at forces, pressures, and flow rates exceeding those which the replaceable injector component can withstand, based on the replaceable injector component's remaining or unused viable life and any identified accumulated distress. As a result, the likelihood that an injector component will fail during use is significantly reduced since the user is alerted when cumulative distress reaches substantial levels. Further, manufacturing and design requirements for the replaceable injector components can be reduced since injector forces can be more accurately matched to maximum levels that the replaceable injector component can withstand. Specifically, reusable components need not be manufactured to withstand maximum injector forces for the entire lifespan of the reusable component, as is currently required.

According to an aspect of the disclosure, a method of monitoring a status of a replaceable component of a fluid injector includes: providing a viable life for a replaceable component of a fluid injector; calculating an accumulated amount of distress experienced by the replaceable component based on each set of previously collected injection parameter data associated with each injection procedure previously performed on one or more patients therewith; determining, based in part on the accumulated amount of distress, a used portion of the viable life that the replaceable component has experienced as a result of the previously performed injection procedures and, therewith, an unused portion of the viable life; and providing to an operator of the fluid injector an indication of at least one of the unused and used portions of the viable life of the replaceable component.

In some examples, the injection parameter data can include one or more of an injection pressure, an injection time, and an injection temperature. The accumulated amount of distress can be calculated using at least an algorithm that employs a model descriptive of material degradation of the replaceable component. The model can be based, for example, on Miner's Rule or on an Inverse Power Law-Weibull Model.

In some examples, the injection parameter data can include data collected from multiple portions of the fluid injector. In addition, providing to the operator of the fluid injector an indication of the unused and/or used portions of the viable life can include displaying a visual representation of the used portion of the viable life relative to the viable life of the replaceable component. The viable life of the replaceable component can be determined before the replaceable component is installed on the fluid injector.

According to another aspect of the disclosure, a fluid delivery system capable of monitoring a replaceable component thereof includes: a fluid injector; at least one replaceable component for use with the fluid injector; a controller; and a visual and/or audio feedback device. The controller can be configured to: obtain a viable life for the at least one replaceable component; calculate an accumulated amount of distress experienced by the replaceable component based on each set of previously collected injection parameter data associated with each injection procedure previously performed on one or more patients using the fluid injector; and determine, based in part on the accumulated amount of distress, a used portion of the viable life that the replaceable component has experienced as a result of the previously performed injection procedures and an unused portion of the viable life. The visual and/or audio feedback device can be configured to provide to an operator of the fluid injector an indication of the unused and/or used portions of the viable life of the replaceable component.

In some examples, the at least one replaceable component comprises a disposable multi-patient fluid path set. In addition, the fluid delivery system can include a sensing or timing device associated with a portion of the fluid injector and configured to collect the injection parameter data.

According to another aspect of the disclosure, a system for monitoring a replaceable component of an apparatus is provided. The system includes: a controller for controlling operation of an apparatus being monitored by the system and programming instructions operably associated with the controller. The programming instructions, when executed, cause the controller to: accept input of a viable life for a replaceable component of the apparatus; calculate an accumulated amount of distress experienced by the replaceable component based on each set of previously collected use data associated with each previous use of the replaceable component by the apparatus; and determine, based in part on the accumulated amount of distress, a used portion of the viable life that the replaceable component has experienced as a result of the previous use or uses thereof and an unused portion of the viable life. The system also includes a visual and/or audio feedback device configured to provide to an operator of the apparatus an indication of at least one of the unused and used portions of the viable life of the replaceable component.

In some examples, the apparatus includes at least one of an infusion device and a centrifuge separator. In that case, the controller can be configured to control operation of the at least one of the infusion device and the centrifuge separator. The replaceable component, which is associated with the infusion device and/or the centrifuge separator, can be at least one of a syringe, a tubing set, a valve, a fluid connector, or any combination thereof.

According to another aspect of the disclosure, a method of monitoring a status of a replaceable component of a fluid injector includes: providing a viable life for the replaceable component; collecting a present set of injection parameter data associated with a planned injection procedure to be performed with the replaceable component; calculating an estimated amount of distress that would be experienced by the replaceable component if the planned injection procedure were to be performed in accordance with the present set of injection parameter data; determining, based in part on the estimated amount of distress, a portion of the viable life that would be experienced by the replaceable component if the planned injection procedure were to be performed and, as a result, the replaceable component were to incur the estimated amount of distress; comparing the viable life of the replaceable component to the portion of the viable life that would be experienced by the replaceable component if the planned injection procedure were to be performed; and providing an indication of a result of the comparison to an operator of the fluid injector.

In some examples, the injection parameter data can include one or more of an injection pressure, an injection time, and an injection temperature. In addition, the estimated amount of distress can be calculated using at least an algorithm that employs a model descriptive of material degradation of the replaceable component. The model can be based, for example, on Miner's Rule or on an Inverse Power Law-Weibull Model.

In some examples, the injection parameter data can include data collected from multiple portions of the fluid injector. In addition, providing an indication of a result of the comparison can include displaying a visual representation of the used portion of the viable life relative to the viable life of the replaceable component. The viable life of the replaceable component can be determined before the replaceable component is installed on the fluid injector.

According to another aspect of the disclosure, a method of monitoring a status of a replaceable component of a fluid injector includes: providing a viable life for the replaceable component; calculating an accumulated amount of distress experienced by the replaceable component based on each set of previously collected injection parameter data associated with each injection procedure previously performed therewith; collecting a present set of injection parameter data associated with a planned injection procedure to be performed with the replaceable component; calculating an estimated amount of additional distress that would be experienced by the replaceable component if the planned injection procedure were to be performed in accordance with the present set of injection parameter data; determining, based in part on the accumulated amount of distress, a used portion of the viable life that the replaceable component has experienced as a result of the previously performed injection procedures and, therewith, an unused portion of the viable life; determining, based in part on the estimated amount of additional distress, an additional portion of the viable life that would be experienced by the replaceable component if the planned injection procedure were to be performed and, as a result, the replaceable component were to incur the estimated amount of additional distress; comparing at least one of the unused and used portions of the viable life of the replaceable component to the additional portion of the viable life that would be experienced by the replaceable component if the planned injection procedure were to be performed; and providing an indication of a result of the comparison to an operator of the fluid injector.

In some examples, the injection parameter data can include one or more of an injection pressure, an injection time, and an injection temperature. The estimated and the accumulated amounts of distress can each be calculated using at least an algorithm that employs a model descriptive of material degradation of the replaceable component. The model can be based, for example, on Miner's Rule or on an Inverse Power Law-Weibull Model. The injection parameter data can include data collected from multiple portions of the fluid injector.

In some examples, providing an indication of a result of the comparison can include displaying a visual representation of the used portion of the viable life relative to the viable life of the replaceable component. The viable life of the replaceable component can be determined, for example, before the replaceable component is installed on the fluid injector.

In some examples, the accumulated amount of distress experienced by the replaceable component will initially be zero when no injection procedure has been previously performed therewith and the planned injection procedure will be intended as the first to be used therewith.

According to yet another aspect of the disclosure, a system capable of monitoring a replaceable component thereof is provided. The system includes: a controller for controlling operation of the system and programming instructions operably associated with the controller. The programming instructions, when executed, cause the system to: accept input of a viable life for a replaceable component of the system; calculate an accumulated amount of distress experienced by the replaceable component based on each set of previously collected use data associated with each previous use of the replaceable component by the system; and determine, based in part on the accumulated amount of distress, a used portion of the viable life that the replaceable component has experienced as a result of the previous use or uses thereof and an unused portion of the viable life. The system also includes a visual and/or audio feedback device configured to provide to an operator of the system an indication of at least one of the unused and used portions of the viable life of the replaceable component.

In some examples, the system is a fluid delivery system comprising a fluid injector. In that case, the use data associated with each previous use of the replaceable component by the system is injection parameter data associated with each injection procedure previously performed on one or more patients using the fluid injector, wherein the injection parameter data includes one or more of an injection pressure, an injection time, and an injection temperature. In addition, the replaceable component can include a syringe, a tubing set, a valve, a fluid connector, a multi-patient fluid path set, a single-patient fluid path set or any combination thereof. The system can also include a sensing or timing device associated with a portion of the fluid injector and configured to collect the injection parameter data.

According to another aspect of the disclosure, a disposable life indicator for measuring cumulative fluid pressure for a fluid injector includes: a fluid collecting portion in fluid communication with a fluid set of a fluid injector; and a gauge configured to indicate to a user a used and/or an unused viable life for a replaceable component of the fluid injector based on a volume of fluid in the fluid collecting portion.

In some examples, the disposable life indicator also includes a check valve disposed between the fluid set of the fluid injector and the fluid collecting portion. The check valve can be configured to permit fluid flow above a threshold pressure to access the fluid collecting portion. The check valve can be a one-way check valve.

In some examples, the disposable life indicator also includes a flow restrictor positioned between the fluid set and the fluid collecting portion for reducing velocity of a fluid flow entering the fluid collecting portion. The flow restrictor can include a porous filter. In addition, the gauge can include a piston moveably disposed within a bore of the gauge and configured to move therethrough as the volume of fluid in the fluid collecting portion increases. The piston can have a conspicuous tip configured to extend beyond an open distal end of the gauge in an end-of-use position. In other examples, the gauge can include a bourdon tube.

These and other features and characteristics of certain and non-limiting embodiments, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

Further features and other objects and advantages will become apparent from the following detailed description made with reference to the drawings in which.

DESCRIPTION

Figure 1:
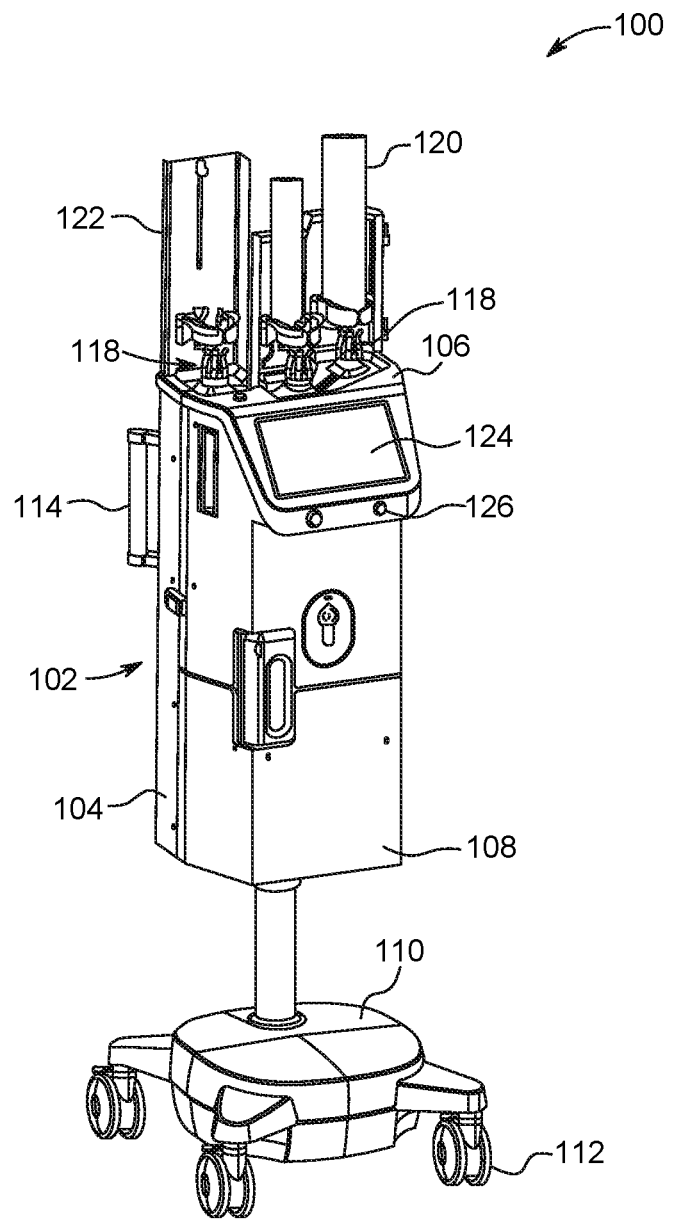
FIG. 1 is a perspective view of a multi-fluid delivery system (referred to herein as "an injector"), according to one aspect of the disclosure.

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

As used herein, the terms "communication" and "communicate" refer to the receipt or transfer of one or more signals, messages, commands, or other types of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, routed, and the like, between the first and second unit or component. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible.

The present disclosure is generally directed to a fluid injector system 100 (shown in FIGS. 1, 2, and 8) and associated monitoring system 10 (shown in FIG. 8) that monitors or tracks the status and remaining or unused viable life of one or more replaceable and disposable components of the injector 100, such as the MUDS, syringes, fluid sources, connectors, valves, and other components (referred to herein collectively as "the replaceable injector components"). The monitoring system 10 provides feedback to an operator thereof about the remaining or unused viable life of the replaceable component(s) and, in certain circumstances, issues an alert if one of the replaceable components reaches the end of its anticipated useful life. The replaceable components are often at least partially formed from plastic materials, which degrade or deform when subjected to substantial force or pressure over time, such as pressure provided as the injector 100 forces fluid through the replaceable injector components. The monitoring system 10 is configured to collect information about injector use and, based on the collected information, estimate and/or determine remaining or unused viable life of a replaceable component based on data from prior injections. As is discussed herein, the monitoring system 10 can control operation of the injector 100 and reduce injection force or entirely prevent an injection from being performed if the replaceable injector components are determined to be unsuitable to withstand an expected injection pressure.

Fluid Injector

Figure 2:
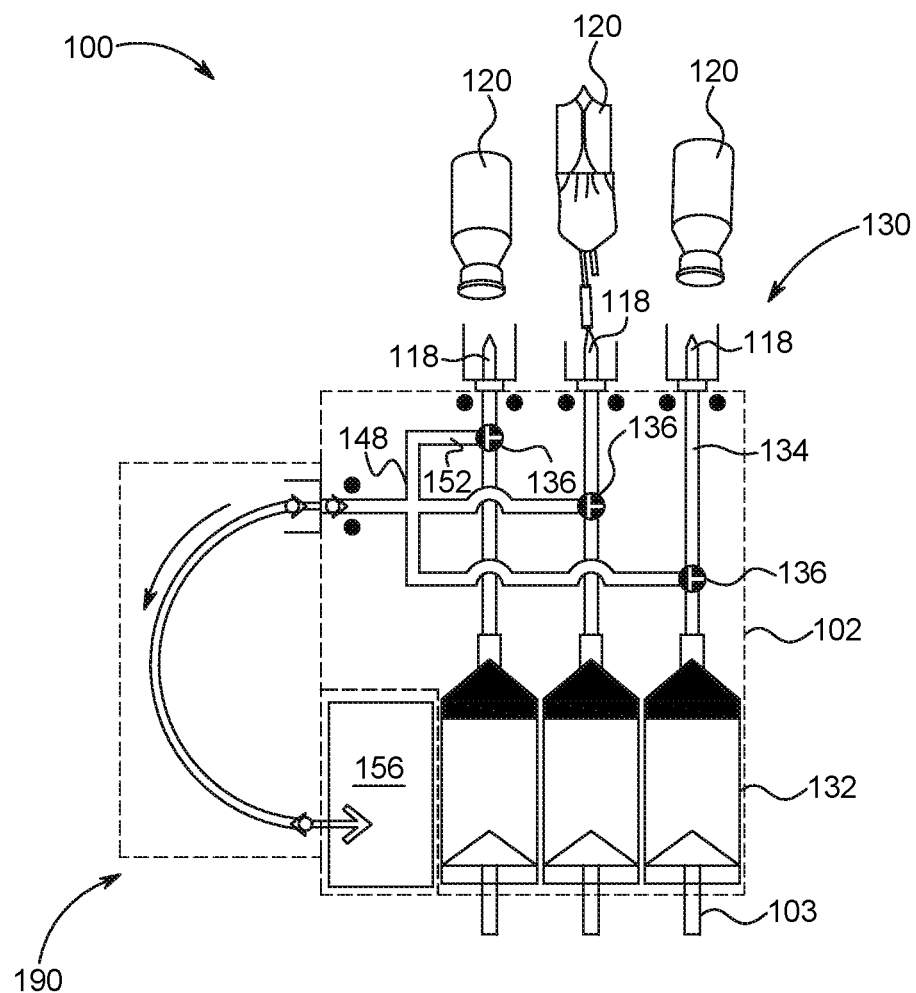
FIG. 2 is schematic view of various fluid paths within the injector of FIG. 1.

With reference to FIG. 1, the fluid injector 100 is configured to deliver fluid to a patient through a MUDS 130 (shown in FIGS. 2 and 8) in fluid communication with a single-use disposable set (SUDS) 190 (shown in FIG. 2). The fluid injector 100 includes an injector housing 102 having opposed lateral sides 104, a distal or upper end 106, and a proximal or lower end 108. In some embodiments, the housing 102 can be supported on a base 110 having one or more wheels 112 for rotatable and movable support of the housing 102 on a floor surface. The one or more wheels 112 can be lockable to prevent the housing 102 from inadvertently moving once positioned at a desired location. At least one handle 114 can be provided to facilitate moving and positioning the fluid injector 100. In other embodiments, the housing 102 can be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices, used to control operation of reciprocally movable piston elements 103 (shown on FIG. 2) associated with the fluid injector 100. Such piston elements 103 can be reciprocally operable via electro-mechanical drive components such as a ball screw shaft driven by a motor, a voice coil actuator, a rack-and-pinion gear drive, a linear motor, and the like. In some embodiments, at least some of the mechanical drive components, electrical and power components, and control components can be provided on the base 110 portion of the injector 100.

The fluid injector 100 includes at least one bulk fluid connector 118 for connection with at least one bulk fluid source 120. In some embodiments, a plurality of bulk fluid connectors 118 can be provided. For example, as shown in FIG. 1, three bulk fluid connectors 118 can be provided in a side-by-side or other arrangement. In some embodiments, the at least one bulk fluid connector 118 can be a spike configured for removably connecting to the at least one bulk fluid source 120, such as a vial, a bottle, or a bag. The at least one bulk fluid connector 118 can have a reusable or non-reusable interface with each new bulk fluid source 120. The at least one bulk fluid connector 118 can be formed on the MUDS 130 (shown in FIG. 2), as described herein. The at least one bulk fluid source 120 can be configured for receiving a medical fluid, such as saline, contrast solution, or other medical fluid, for delivery to the fluid injector system 100. The housing 102 can have at least one support member 122 for supporting the at least one bulk fluid source 120 once it is connected to the fluid injector system 100.

With continued reference to FIG. 1, the fluid injector system 100 includes one or more user interfaces 124, such as a graphical user interface (GUI) display window. The user interface 124 can display information pertinent to a fluid injection procedure performed by the fluid injector 100, such as current flow rate, fluid pressure, and volume remaining in the at least one bulk fluid source 120 connected to the fluid injector 100, and can be a touch screen GUI that allows an operator to input commands and/or data for operation of the fluid injector system 100. While the user interface 124 is shown in FIG. 1 on the injector housing 102, the user interface 124 can also be in the form of a remote display that is wired or wirelessly linked to the housing 102 and can control mechanical elements of the fluid injector 100. In some embodiments, the user interface 124 can be a tablet that is detachably connected to the housing 102 and is in wired or wirelessly linked communication with the housing 102. Additionally, the fluid injector system 100 and/or user interface 124 can include at least one control button 126 for tactile operation by an attendant operator of the fluid injector system 100.

Having generally described the injector 100, the MUDS 130, which is configured to be removably connected to the fluid injector 100 will now be discussed in detail. With reference to FIG. 2, the MUDS 130 delivers one or more fluids from the one or more bulk fluid sources 120 to the patient. The MUDS 130 can include one or more syringes 132 and piston elements 103. In some embodiments, the number of syringes 132 can correspond to the number of bulk fluid sources 120. For example, with reference to FIG. 2, the MUDS 130 has three syringes 132 in a side-by-side arrangement such that each syringe 132 is fluidly connectable to one of the bulk fluid sources 120. In some embodiments, one or two bulk fluid sources 120 can be connected to one or more syringes 132 of the MUDS 130. Each syringe 132 can be fluidly connectable to one of the bulk fluid sources 120 by a corresponding bulk fluid connector 118 and an associated MUDS fluid path 134. The MUDS fluid path 134 can have a spike element that connects to the bulk fluid connector 118. In some embodiments, the bulk fluid connector 118 can be provided directly on the MUDS 130.

The MUDS 130 can include one or more valves 136, such as stopcock valves, for controlling which medical fluid or combinations of medical fluids are withdrawn from the multi-dose bulk fluid source 120 and/or are delivered to a patient through each syringe 132. In some embodiments, one or more valves 136 can be provided either on the syringe 132 or on a manifold 148. The manifold 148 can be in fluid communication via valves 136 and/or syringes 132 with a first end of the MUDS fluid path 134 that connects each syringe 132 to the corresponding bulk fluid source 120. The opposing second end of the MUDS fluid path 134 can be connected to the respective bulk fluid connector 118 that is configured for fluidly connecting with the bulk fluid source 120.

With continued reference to FIG. 2, in some embodiments, the fluid outlet line 152 can also be connected to a waste reservoir 156 on the fluid injector system 100. The waste reservoir 156 is desirably separate from the syringes 132 to prevent contamination. In some embodiments, the waste reservoir 156 is configured to receive waste fluid expelled from the syringes 132 during, for example, a priming operation. The waste reservoir 156 can be removable from the housing 102 in order to dispose of the contents of the waste reservoir 156. In other embodiments, the waste reservoir 156 can have a draining port (not shown) for emptying the contents of the waste reservoir 156 without removing the waste reservoir 156 from the housing 102. In some embodiments, the waste reservoir 156 is provided as a separate component from the MUDS 130.

Disposable Life Indicators

Having described the fluid injector 100 and MUDS 130, with reference to FIGS. 3A-7, a disposable life indicator 50, which can be associated with, connected to, or integrally formed with a portion of the replaceable component, such as the MUDS fluid path 134, will now be discussed in detail. The disposable life indicator 50 can be attached to a port 52 extending from the fluid path 134 and in fluid communication with the fluid path 134 through a narrow channel 54 (shown in FIGS. 3B and 4B). The port 52 can include any suitable connector, as is known in the art, for connecting the indicator 50 to the fluid path 134 including, but not limited to, a luer connector, a snap fit connector, threaded connectors, or combinations thereof. The disposable life indicator 50 is a mechanical device or mechanism configured to indicate to a user or injector operator a cumulative pressure exerted on the replaceable component, such as the MUDS 130, and, in particular, to indicate to the user or injector operator when the replaceable component reaches the end of its lifecycle and should be replaced. In general, the disposable life indicator 50 includes an advancing structure, such as a piston or dial, which transitions from a full or unused position, indicating that the replaceable component is unused and in a like-new condition, to an empty or end-of-use position, indicating that the replaceable component has been exposed to maximum cumulative fluid pressure and should be replaced. The user or injector operator is instructed to remove and replace the replaceable component when the advancing structure is in its end-of-use position. The disposable life indicator 50 can be a single use disposable device that is replaced at the same time as the replaceable component.

Figure 3A:
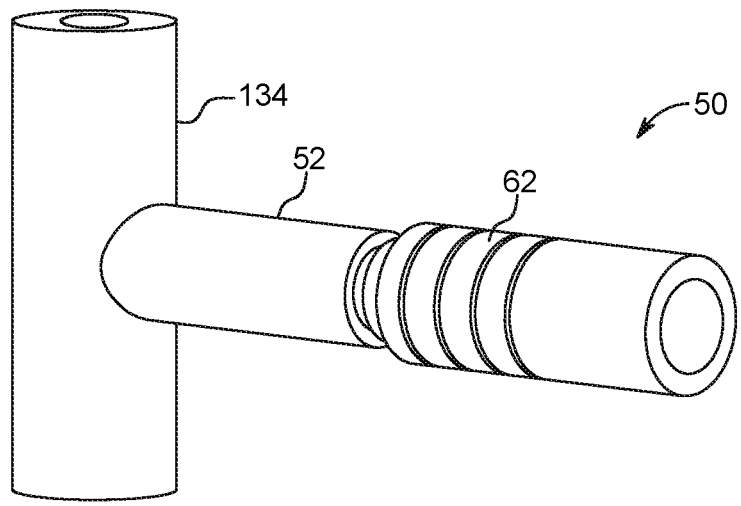
FIG. 3A is a perspective view of a life indicator, in a full or unused position, connected to a fluid path set, according to an aspect of the disclosure.
Figure 3B:
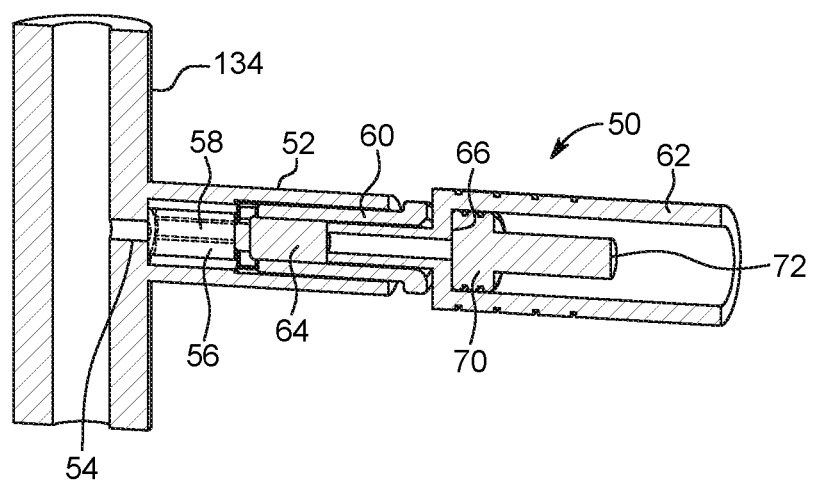
FIG. 3B is cross section view of the life indicator and fluid path set of FIG. 3A in a full or unused position.
Figure 4A:
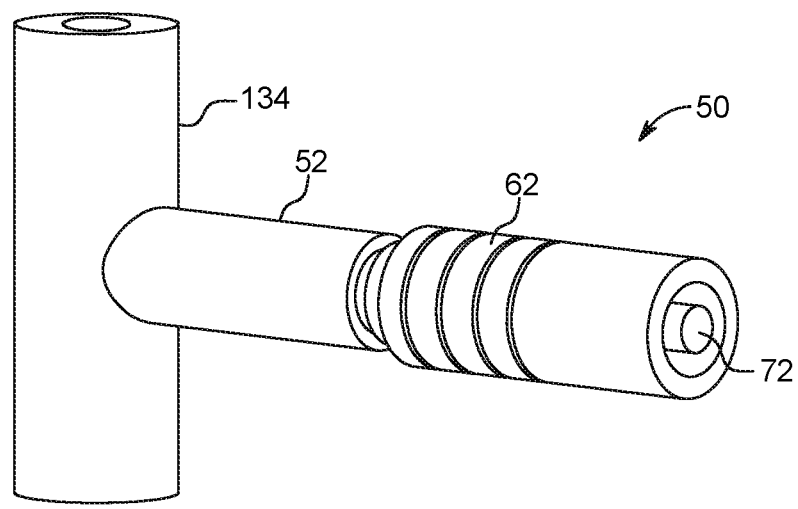
FIG. 4A is a perspective view of the life indicator of FIG. 3A in an end-of-life position.
Figure 4B:
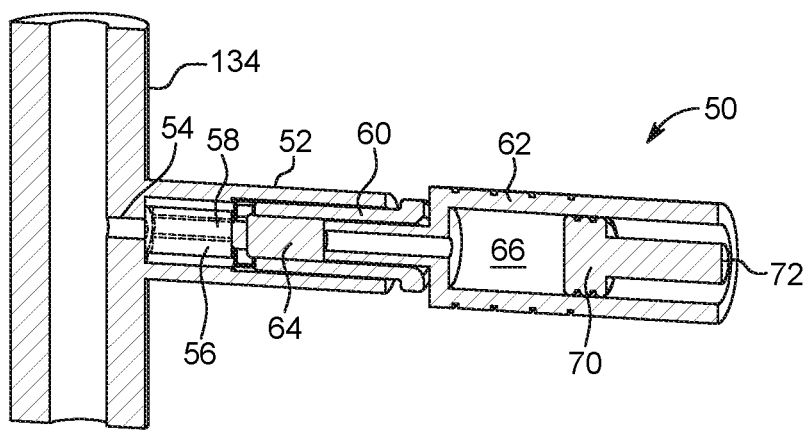
FIG. 4B is a cross section view of the life indicator of FIG. 4A in the end-of-life position.

With specific reference to FIGS. 3B and 4B, in one embodiment, the life indicator 50 is inserted in and extends from the port 52, and includes a gauge 62 with a piston 70 positioned therein to move within a bore of, or through a barrel of, the gauge 62 to indicate cumulative pressure. The indicator 50 includes a high pressure one-way check valve 56, such as an elastomeric cylinder, defining an inner channel 58 seated against a proximal end of the retainer 60. The valve 56 prevents fluid at low pressure from entering the indicator 50. Specifically, since low pressure fluid flows have negligible effect on the structural integrity of the replaceable component or MUDS 130, the check valve 56 is configured to prevent such low pressure fluid flows from contributing to advancement of the piston 70. The check valve 56 is configured to open at a threshold pressure, which is a pressure sufficient to affect the replaceable component, and to prevent lower pressure fluid flows from passing through the valve 56.

The retainer 60, such as an insert or housing, includes a hollow cylindrical portion for receiving the gauge 62 of the life indicator 50, and is positioned adjacent to and/or pressed against the check valve 56. A flow restrictor 64 is inserted in a proximal end of the retainer 60. The flow restrictor 64 is provided to disrupt high pressure fluid flows from entering the gauge 62 of the indicator 50 to prevent distress to the gauge 62 from fluid flowing through the check valve 56. For example, the flow restrictor 64 can be a porous filter with a plurality of tortuous flow passages. Directing fluid through the tortuous passages reduces flow rate as the fluid advances towards the gauge 62.

The gauge 62 is at least partially received in the retainer 60 and extends from a distal end thereof. The gauge 62 includes a fluid collecting portion 66 at a proximal end thereof, and a movable indicating structure, such as the piston 70, which is slideably received within the barrel/bore of the gauge 62. The piston 70 advances through the barrel of the gauge 62 as fluid collects in the fluid collecting portion 66. The piston 70 can have a conspicuous end-of-use portion 72, such as a colored tip, that is configured to extend from the barrel of the gauge 62 and thus is easily visible when the maximum cumulative pressure is reached and/or exceeded. In some embodiments, the gauge 62 can include various graduations or markings (not shown in FIGS. 3A-4B) for showing how far the piston 70 has advanced through the gauge 62. For example, markings can indicate to the injector operator an estimated number of injections remaining before the replaceable component must be replaced, an estimated total number of injections performed already, or other relevant information. Alternatively, in some embodiments, the gauge 62 can be an electronic volume sensor configured to measure fluid collected in the fluid collecting portion 66 of the gauge 62. A signal from the volume sensor can be sent to a controller or user interface of the injector for providing data to the operator regarding cumulative pressure level.

In other embodiments, the gauge 62 can include an electronic indicator. For example, the gauge 62 can include a light, such as an LED bulb, configured to light up when the piston 70 reaches its end-of-use position. The electronic indicator or LED bulb can be located on the life indicator 50, on the fluid injector 100, or at a remote location. Further, graduations or markings on the gauge 62 barrel can include electronic indicators, such as LED bulbs, configured to light up when the piston 70 reaches a particular position within the gauge 62. In other embodiments, the electronic indicator can be a verbal or audio indicator, such as an alarm that sounds when the piston 70 advances to the end-of-use position and should be replaced.

In use, as pressurized fluid flows through the MUDS fluid path 134, a small volume of fluid is diverted into the narrow channel 54 of the port 52 and toward the gauge 62. If the fluid flow is sufficient to open the one-way check valve 56, fluid passes through the valve 56 and into the retainer 60. The fluid is prevented from flowing back into the MUDS fluid path 134 by the valve 56. After passing through the valve 56, the fluid is directed though the flow restrictor 64 and into the fluid collecting portion 66 of the gauge 62. As the volume of collected fluid increases, the piston 70 is driven through barrel of the gauge 62, thereby providing a cumulative indication of pressure exerted on the replaceable or disposable injector component. It is noted that when low pressure fluid flow passes through the MUDS fluid path 134, the valve 56 remains closed and no new fluid is provided to advance the piston. As shown in FIGS. 3A and 3B, in the unused or full position, the piston 70 is initially seated against the proximal end of the gauge 62. As fluid volume in the fluid collecting portion 66 increases, the piston 70 is driven through the gauge 62 toward the distal end thereof. As shown in FIGS. 4A and 4B, in the end-of-use position, the end-of-use portion 72 extends beyond the distal end of the gauge 62.

Figure 5:
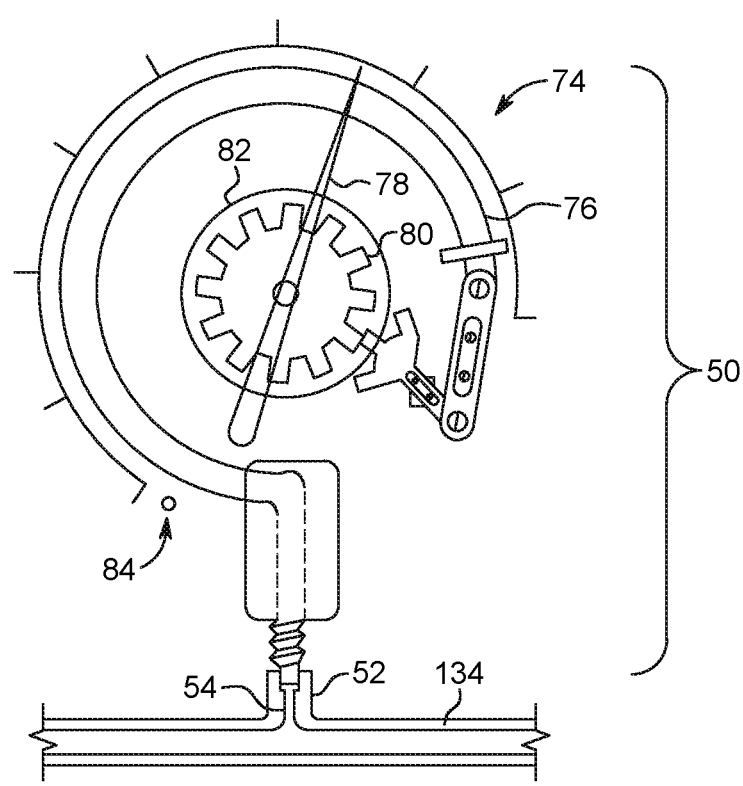
FIG. 5 is a schematic drawing of a bourdon tube life indicator according to another aspect of the disclosure.

With specific reference to FIG. 5, in another embodiment of the indicator 50, the gauge is a bourdon tube arrangement 74. The bourdon tube arrangement 74, which resembles a standard gas gauge for a gasoline powered vehicle, includes a flexible tube 76 and an arm 78 driven by a pinion 80 and biasing spring 82. The pinion 80 and biasing spring 82 are pivotally engaged to the tube 76. A proximal end of the tube 76 is connected to and receives pressurized fluid from the MUDS fluid path 134 through the narrow channel 54 of the port 52. As the volume of pressurized fluid in the tube 76 increases, the tube 76 exerts a force on the pinion 80 and biasing spring 82 causing the arm 78 to transition from the unused or full position to the empty or end-of-life position. A stop 84 located adjacent to the proximal end of the tube 76 indicates when the reusable component reaches the end of its expected life.

In addition to the above-described piston and bourdon tube mechanisms, the indicator 50 can include other electronic or mechanical mechanisms or devices or gauges, as are known in the art, for indicating that fluid is being collected from the fluid path 134. For example, the mechanism can be an inflatable balloon. As the injector is in use, fluid collects in the balloon. The balloon is permitted to continue to expand until a particular size or inflation level is obtained, which signifies end-of-use for the replaceable component. In another embodiment, a coiled balloon or tube, such as a party horn, can be configured to unfurl as fluid collects therein. The horn can be configured such that when the horn portion is fully uncurled, the replaceable component has reached the end of its useful life and should be replaced.

Figure 6:
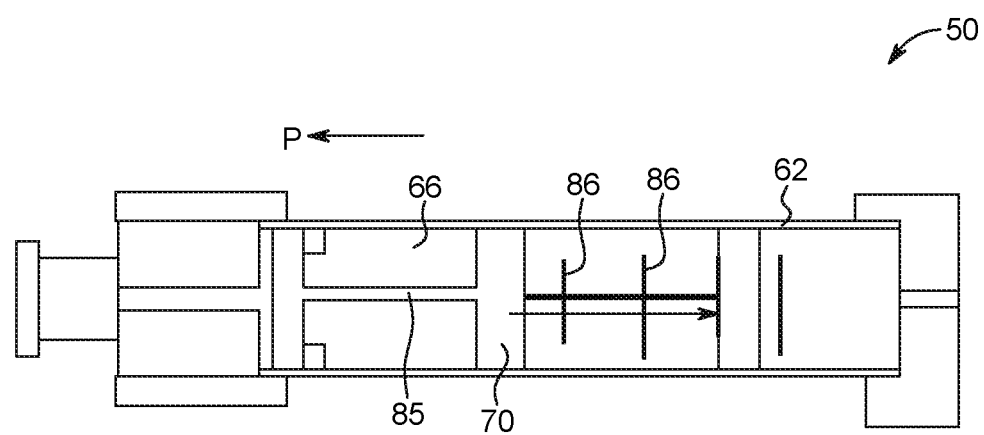
FIG. 6 is a schematic drawing of a life indicator according to another aspect of the disclosure.
Figure 7:
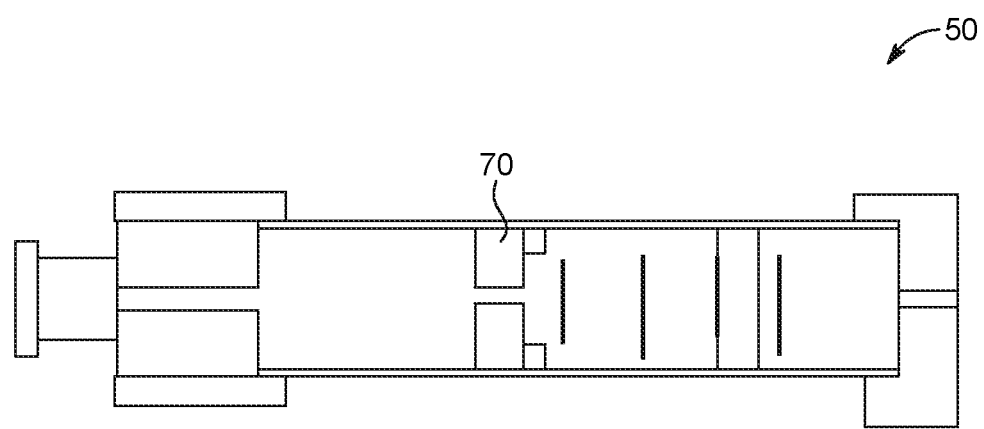
FIG. 7 is a schematic drawing of a life indicator according to another aspect of the disclosure.

With reference to FIG. 6, in another embodiment, the indicator 50 can include an elastic (e.g., stretchable) member 85 connected to a piston or plunger 70 for slowing the advancement of the piston or plunger 70 through a gauge 62. For example, the elastic member 85 can be anchored to a proximal portion of the gauge 62 and configured to bias the piston or plunger 70 in the proximal direction P. In this way, the elastic member 85 restricts advancement of the piston or plunger 70 toward the end-of-use position. Therefore, more fluid must collect in the fluid collecting portion 66 of the gauge 62 before the piston or plunger 70 begins to advance. As in previously-described embodiments, the elastic member 85 can be tuned to the life cycle for a particular replaceable component of the injector. For example, for replaceable components with relatively short lifecycles, the elastic member 85 can only slightly bias the piston or plunger 70 so that the piston or plunger 70 freely advances through the gauge 62. For replaceable components with particularly short lifecycles, the indicator 50 may not include any anchor or stretchable component at all for the piston or plunger 70, as shown, for example, in FIG. 7.

With continued reference to FIG. 6, for replaceable components with longer lifecycles, the elastic member 85 can be more resistant to deformation, meaning that more force must be applied by pressurized fluid before the piston or plunger 70 advances. The gauge 62 can include translucent or transparent portions so that the injector operator can see how far the piston or plunger 70 has advanced. The piston or plunger 70 can also be a bright color so that it is easily identified by the injector operator. Markings 86, such as graduations, can be provided on the gauge 62. The markings 86 can be used to indicate how much time (e.g., number of injection cycles) are left until the piston or plunger 70 reaches the end-of-use position indicating that the replaceable component needs to be replaced.

In other embodiments, the disposable life indicator 50 can be replaced with an electronic sensor for measuring the fluid pressure (e.g., a maximum or average fluid pressure) for each injection performed using the replaceable injector component. For example, a high pressure sensor can be connected to the port 52 and placed in fluid communication with the MUDS fluid path 134. The pressure sensor can determine fluid pressure for fluid flowing through the MUDS fluid path 134. The pressure sensor can include a wired connection or a wireless transmitter, such as a short range data transmitter using BLUETOOTH®, for sending a signal from the sensor to a controller or user interface device. The controller or user interface device can provide information, such as the measured pressure of the injection and information about the unused viable life of the injector component to the system operator. A suitable pressure sensor that can be connected to the MUDS fluid path 134 and used to determine lifespan for replaceable injector components is disclosed in U.S. patent application Ser. No. 13/798,709 to Riley et al., which published as Publication No. 2013/0255390 (hereinafter "the '390 publication), and which is incorporated by reference herein in its entirety. As will be discussed in greater detail hereinafter, the measurements recorded by the high pressure sensor can be used to calculate the unused viable life for replaceable components of the injector. The collected measurements and calculated lifespan information can be presented to the user or system operator through a user interface, such as an audio or visual display.

In another embodiment, the injector component is formed from a chromogenic plastic configured to change color or tint over time when exposed to a chemical, such as saline or contrast, or from lack of exposure to oxygen. In this way, the color or tint of the plastic material of the injector component changes a small amount each time that injection fluid is passed through the injector component. The system operator can observe the injector component prior to performing an injection. If the system operator determines that the injector component has changed color a sufficient degree, the operator replaces the component with a new one. Alternatively, the injector can include optical sensors configured to automatically identify a color change in an injector component. When a sufficient color change is identified, the injector can instruct the operator to replace the injector component.

In another embodiment, an indicator can include a conductive portion that is exposed to a weak electrical charge. As in previously described embodiments of the indicator, the conductive portion is exposed to fluid passing through the fluid set. The combination of the weak electrical charge and chemical components of the fluid causes a color change response or reaction, such as oxidation, in the conductive polymer portion of the indicator.

Injector Monitoring System

Having described the fluid injector system 100, replaceable components, such as the MUDS 130, and disposable life indicators 50, the monitoring system 10 with automated and/or electronic components for monitoring and providing feedback about the status of replaceable components will now be discussed in detail.

Figure 8:
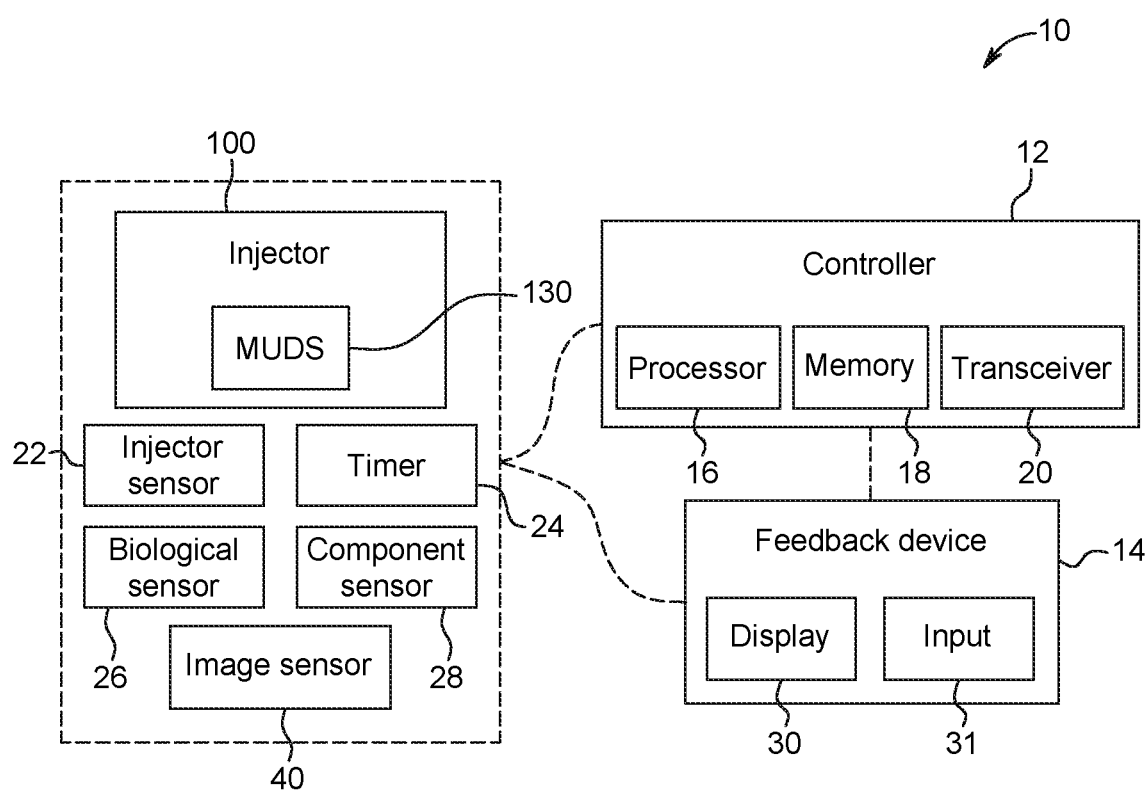
FIG. 8 is a schematic drawing of a fluid delivery system including the injector of FIG. 1, according to an aspect of the disclosure.

With reference to FIG. 8, the monitoring system 10 includes a controller 12 or computing unit, and a feedback device 14. The controller 12 and feedback device 14 can be a part of the fluid injector 100 and, for example, located in the injector housing 102. Alternatively, the controller 12 and feedback device 14 can be one or more independent electronic devices remote from and in communication with the injector 100. The feedback device 14 includes a user input 31 for obtaining information from a system operator, and a display 30 for displaying information, such as results obtained from the predictive life algorithm performed by the controller 12, to the injector operator.

The controller 12 includes a processor 16 with electronic circuitry capable of performing calculations according to instructions stored on computer readable memory 18 associated with the processor 16 or provided to the processor 16 from some external source. The processor 16 can also issue instructions and/or requests for information to other electronic devices, such as sensors, remote electronic databases, data sources, or to the injector 100 for controlling operation thereof. The controller 12 can be integrated with the injector 100 and, for example, can be configured to perform some or all of the functions of the electronic control device that controls operation of the injector 100. As described above, the controller 12 can also be a remote device such as a dedicated electronic device, portable computer, or tablet PC. In that case, the controller 12 can include either a wired connection to the injector 100 or a wireless antenna/transceiver 20 for sending data and instructions between the injector 100 and controller 12.

The monitoring system 10 can also include one or more sensors 22, such as the high pressure sensor described above and disclosed in the '390 publication, for measuring fluid delivery data of the injector 100 during fluid injection. Fluid delivery data can include injection pressure (e.g., maximum fluid pressure) or injection temperature. The monitoring system 10 can also include a timer 24 for measuring duration of an injection. For example, the timer 24 can include a sensing portion configured to identify when fluid flows through the replaceable injector component, and which is also configured to measure a cumulative fluid flow time. The sensing portion can be in fluid connection with the fluid set or, in other embodiments, can include sensors that identify fluid flow indirectly and without direct fluid contact. For example, the sensing portion can be a vibration sensor for measuring vibrations of flexible tubing or other disposable components, optical sensors for measuring changes due to light diffraction when fluid is present and flowing through translucent flexible tubing, or sensors for measuring swell of disposable components as fluid passes through the component. Information from the sensors 22 and/or timer 24 is provided to the controller 12 for collecting, recording, and analyzing data from a fluid delivery procedure. In other embodiments, fluid delivery data can be provided to the controller 12 directly from the electronic control device of the injector 100. For example, the controller 12 can determine fluid delivery data based on the injector settings used for the injection.

With continued reference to FIG. 8, the monitoring system 10 can also include biological sensors 26, such as conductivity sensors, electrochemical sensors, ion sensors, and the like, configured to identify contamination in fluid. The biological sensors 26 are in fluid communication with the replaceable injector components. For example, the biological sensors 26 can be positioned in one of the fluid reservoirs or in the fluid path set of the MUDS 130. The biological sensors 26 can be configured to provide periodic measurements of fluid quality. If contamination is identified, an alert can be provided to the system operator with the feedback device 14. In addition, the injector 10 can be configured not to perform an injection until the contamination alert is addressed.

The monitoring system 10 can also include a number of component verification or confirmation sensors 28 (referred to as "component sensors 28") positioned throughout the MUDS 130. The component sensors 28 are configured to automatically identify codes or labels affixed to the replaceable components (e.g., connector tubing, syringe barrel, or stop cock valve) and to verify that the components are correctly installed and suitable for use with the injector 100. For example, the label could include a barcode embedded with information about the component, including the model number, injection parameter limits, and other information for each component. In that case, the component sensor 28 can be an image or optical sensor that reads the barcode and extracts information therefrom. In some embodiments, the controller 12 can be configured to prevent the injector 100 from performing an injection unless each disposable injector component is verified as being suitable (e.g., correct size and pressure tolerance) for the injection being performed. Alternatively, the controller 12 can provide an alert to the system operator that a component cannot be verified, but give the operator the ability to override the alert and perform the injection if, for example, the operator manually identifies that the component is acceptable.

The controller 12 is configured to monitor or track the remaining or unused viable life of replaceable injector components, such as the MUDS 130, based on one or more predictive disposable life algorithms. The algorithm can be stored on the computer readable memory 18 associated with the controller or provided to the controller 12 from an external source. The algorithms estimate or determine the amount of stress/strain forces (referred to herein as "the accumulated distress") that the replaceable injector component has been subjected to and, based on an estimate of the viable life of the replaceable component (i.e., an estimate of the total amount of stress/strain forces that the replaceable component can withstand before failure), provides an estimate of remaining or unused viable life (i.e., an unused portion of the viable life). In some embodiments, the algorithm is based on one or more models for demonstrating material degradation of a structure. For example, the disposable predictive life algorithm can be based on Miner's Rule, which estimates that there is a linear relationship between the number of cycles (e.g., the number of times a force is applied to an object) and the stress applied during each cycle. Miner's Rule is represented by the following equation:

$$\frac{\sum_{i=1}^{k} n_i \times S_i}{W_{Failure}} = C$$

In the above equation, $n_i$ is the number of cycles and $S_i$ is the stress amount for each cycle. $W_{Failure}$ is the total amount of stress that the system can withstand prior to failure. C is the fraction of life consumed by the exposure to the $n_i$ stress cycles. In the case of calculations using Miner's Rule, experimental results demonstrating the failure stress W must be provided. The controller 12 can obtain these experimental values for the replaceable injector component from a lookup table or computer database. Other non-linear models, such as an inverse power Law-Weibull model, can also be used for purposes of determining cumulative distress and unused viable life for the replaceable injector components.

Figure 9A:
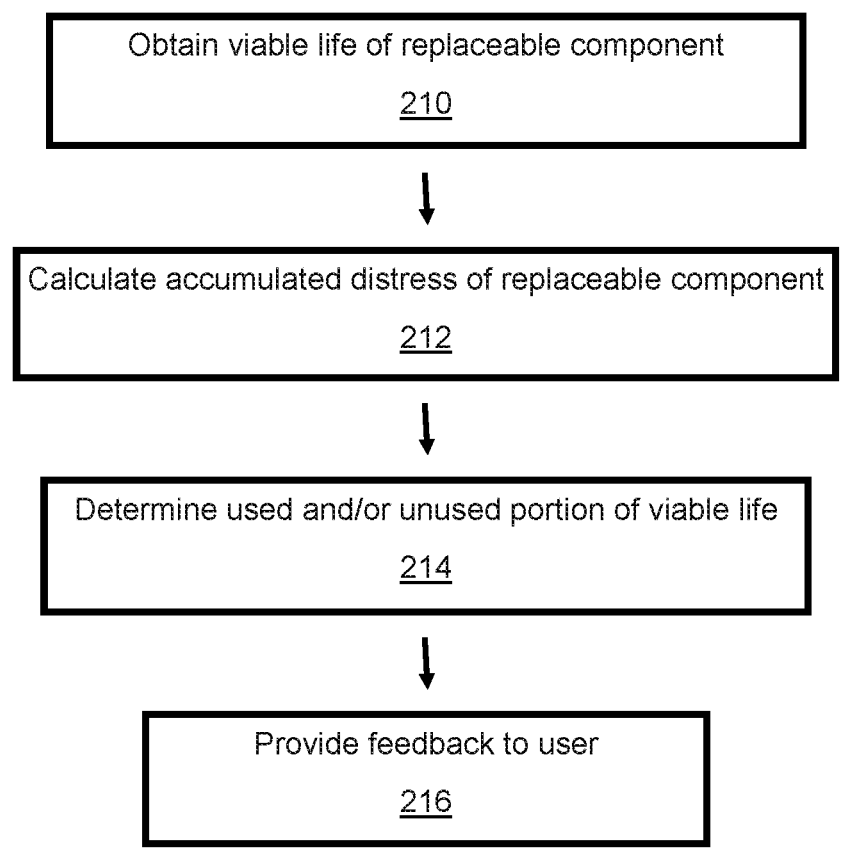
FIG. 9A is a flow chart illustrating steps for monitoring a fluid delivery system, according to an aspect of the disclosure.

With reference to FIG. 9A, the controller 12 can be configured to perform the following actions or steps to calculate used and/or unused viable life of a replaceable component and for providing the calculated information to a user.

In one example, as shown in box 210, the controller 12 obtains information indicative of a viable life of a replaceable component of an injection system. For example, a user can manually enter the viable life for a replaceable component to the controller 12. Alternatively, the viable life can be automatically obtained by the controller 12, such as, for example, by downloading viable life for a component of interest from an external electronic device, system, or computer database. In other examples, the controller 12 can calculate viable life based, for example, on the geometry, material properties, location within the injector (e.g. proximity to a fluid pump or syringe), or function of the replaceable component of interest.

As shown in box 212, the controller 12 next calculates an accumulated amount of distress experienced by the replaceable component. The algorithm for calculating accumulated distress can be a simple linear relationship based only on injection force and number of injection cycles. Alternatively, more complex modeling algorithms taking into account the physical and material properties of the injector component, temperature, and other properties and parameters can also be used within the scope of the present disclosure.

The accumulated amount of distress can be based on one or more sets of previously collected injection parameter data associated with each injection procedure previously performed on one or more patients with the fluid injection system. Injection parameter data can include information about an injection, such as maximum or average fluid pressure during the injection, the flow rate, the volume of the fluid, the temperature of the fluid, the duration of the injection, as well as any other information indicative of the stress/strain exerted on the replaceable component of interest during an injection.

The injection parameter data can also include, for example, data about physical, material, and geometric properties of the replaceable component. The geometric property data can include, for example, information about the size and shape of the fluid container or fluid path set, such as inner and outer diameters, length, wall thickness, tensile strength, mass, and/or volume thereof.

The material property data can include, for example, information about the formulation and type of polymer used to form the disposable injector component. In addition to considering material property data about the polymer material that forms the disposable injector component, fluid property data, such as fluid viscosity or concentration, for the fluid being injected, can also be considered by the algorithm.

The geometric, material, and fluid property information can be obtained from a variety of sources. For example, property information can be embedded on a label, bar code, QR code, or other computer readable indicator and extracted by the component sensors 28 as described above. The label or indicator can also point to a specific location in a lookup table or computer database where useful information can be obtained.

The accumulated distress value can be provided in various forms including, for example, a distress value or index representing a percentage or amount of degradation for the component of interest. Alternatively, accumulated distress could be provided as a cumulative amount of force or pressure exerted on the replaceable component by previous injections. In any case, the calculated accumulated distress data can be stored in computer readable memory associated with the controller 12. The controller 12 can update these stored values following each injection to provide a cumulative value corresponding to total distress to the component.

Information included on the label or in the lookup table and relied on by the controller 12 to calculate accumulated distress can also be used to ensure that the injector component and fluid to be injected are suitable for use. For example, the controller 12 can monitor how long a particular bulk fluid container has been opened or an expiration date for the fluid contained therein. The controller 12 can be configured to provide an appropriate warning to a system operator when the fluid to be injected has expired or is otherwise unsuitable for the injection being performed. Similarly, the controller 12 can monitor physical parameters of the injector component and confirm that they are suitable for the injection being performed.

As shown in box 214, a used portion and/or an unused portion of the viable life for the replaceable component can be determined based on the viable life of the replaceable component, as obtained at box 212, and the accumulated amount of distress, as calculated at box 214. In particular, the unused viable life for the replaceable component is exhausted as accumulated distress increases.

As shown in box 216, feedback about the used and/or unused viable life for the replaceable component is provided to the user. For example, feedback can be provided to the user with the visual and/or audio display device 30 (shown in FIGS. 8 and 10). The display device 30 can be the same display used to show the graphical user interface for the injector 100. Alternatively, the display can be provided on a remote electronic device, such as a computer, tablet PC, smartphone, or dedicated electronic device. Based on the feedback, the user can determine when the replaceable component should be replaced and, if necessary, replace the component prior to performing another injection.

In some examples, the system operator can manipulate the display device 30 with a user input 31 (shown in FIG. 8) to select the type of information available and how the information is displayed. For example, a user can select to view a graphical representation of used and/or unused viable life for the replaceable component, for example, in the form of a gas gauge icon or bar graph.

Alternatively or in addition to graphical feedback, feedback can be provided in the form of numerical representations of used and/or unused viable life. For example, used and/or unused viable life can be provided as a percentage of viable life remaining. Alternatively, used and/or unused viable life can be provided as a predicted amount of time until the component should be replaced (e.g., the disposable injector component will need to be replaced in three days) or a number of injections that can be performed before the disposable injector component will need to be replaced. These values can be shown as numerical results and/or with colors indicating injector status. For example, a status indicator or icon can be a green color to signify that the injector is operating normally and that no components will need to be replaced in the short term. Yellow indicates that the replaceable component of interest is nearing the end of its lifecycle and should be replaced soon. Red indicates that the unused viable life of the replaceable component is nearly exhausted and that the replaceable component should be replaced prior to performing another injection.

In other embodiments, the controller 12 and/or display device 30 can also be configured to provide a warning, alarm, or alert if the unused portion of the viable life of the component is nearly exhausted. For example, the display device 30 can provide an audible alarm or flashing icon to inform the operator that the component should be replaced before another injection is performed. Similarly, the controller 12 can be configured to review programmed inputs for an injection (e.g., injection pressure and/or flow rate) and to evaluate whether the programmed inputs are too robust for the replaceable injector components based on the cumulative distress endured thus far and unused viable life of the components. If the programmed inputs are too great for the injector, the injector and/or feedback device can alert the user to replace the replaceable injector components before performing the injection. If the system operator attempts to perform the injection without replacing the component, the controller 12 can automatically reduce programmed inputs to suitable levels to ensure that the injection is performed safely.

Figure 9B:
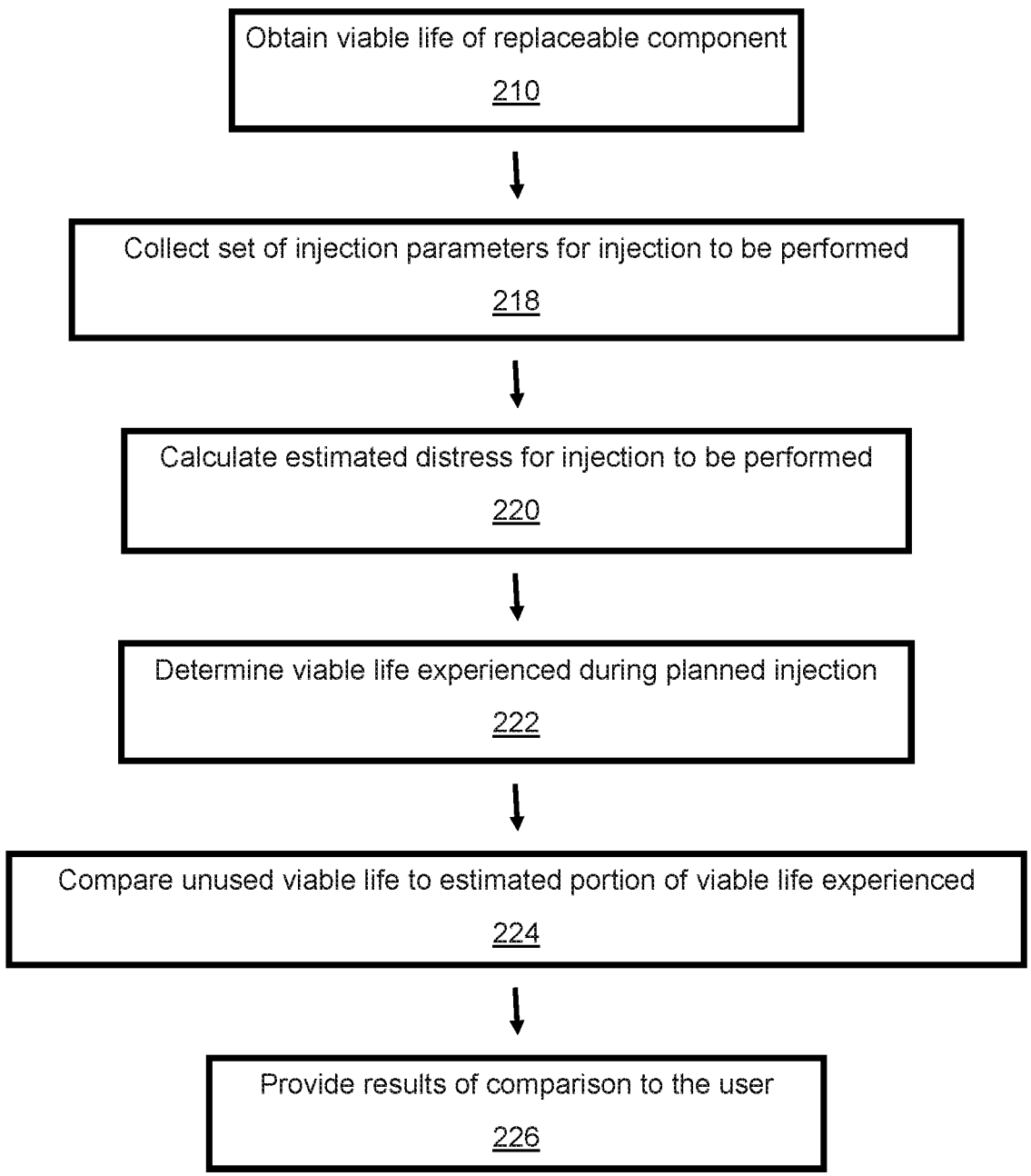
FIG. 9B is a flow chart illustrating steps for monitoring a fluid delivery system in which a first (e.g., a sole or present) use of a replaceable component is considered.

With reference to FIG. 9B, a flow chart illustrating a method for monitoring a present or planned use of a replaceable component of an injector is illustrated. As shown in FIG. 9B, the controller 12 can be configured to provide an indication of whether the unused viable life of a replaceable component of a fluid injector system is sufficient for performing a planned injection procedure. As in the previously described example, the viable life of the replaceable component is provided to the controller 12, as shown at box 210.

As shown at box 218, a present set of injection parameters is provided to the controller. As discussed above, injection parameters can include information about an injection, such as maximum or average fluid pressure during the injection, anticipated flow rate, injection duration, or temperature of the fluid being injected, as well as any other information indicative of the stress/strain exerted on the replaceable component of interest during an injection.

As shown at box 220, the controller 12 calculates an estimated amount of distress that would be experienced by the replaceable component if an injection procedure were performed in accordance with the injection parameters received at box 218. As shown at box 222, the estimated amount of distress is used to determine a portion of the viable life that would be experienced by the replaceable component if the planned injection procedure were performed. As shown at box 224, the unused portion of viable life of the replaceable component can be compared to the viable life that would be experienced by the replaceable component if the planned injection procedure were to be performed to determine, for example, if the replaceable component is suitable for the planned injection. As shown at box 226, the results of the comparison are provided to the user. For example, the results could include a simple message to the user indicating either that the injection can be performed (e.g., an indication that the injector is ready for injection) or that the component should be replaced prior to performing the injection. In other examples, the results can include detailed numerical results, including the estimated distress experienced during the injection, unused viable life of the replaceable component, and/or estimated time or number of injections until the component should be replaced. In other examples, the system can provide an audible alarm informing the user that the replaceable component is not suitable for a planned injection. In other examples, the controller 12 can be configured to prevent an injection from begin performed if the unused viable life of the component is not sufficient for the planned injection.

Figure 9C:
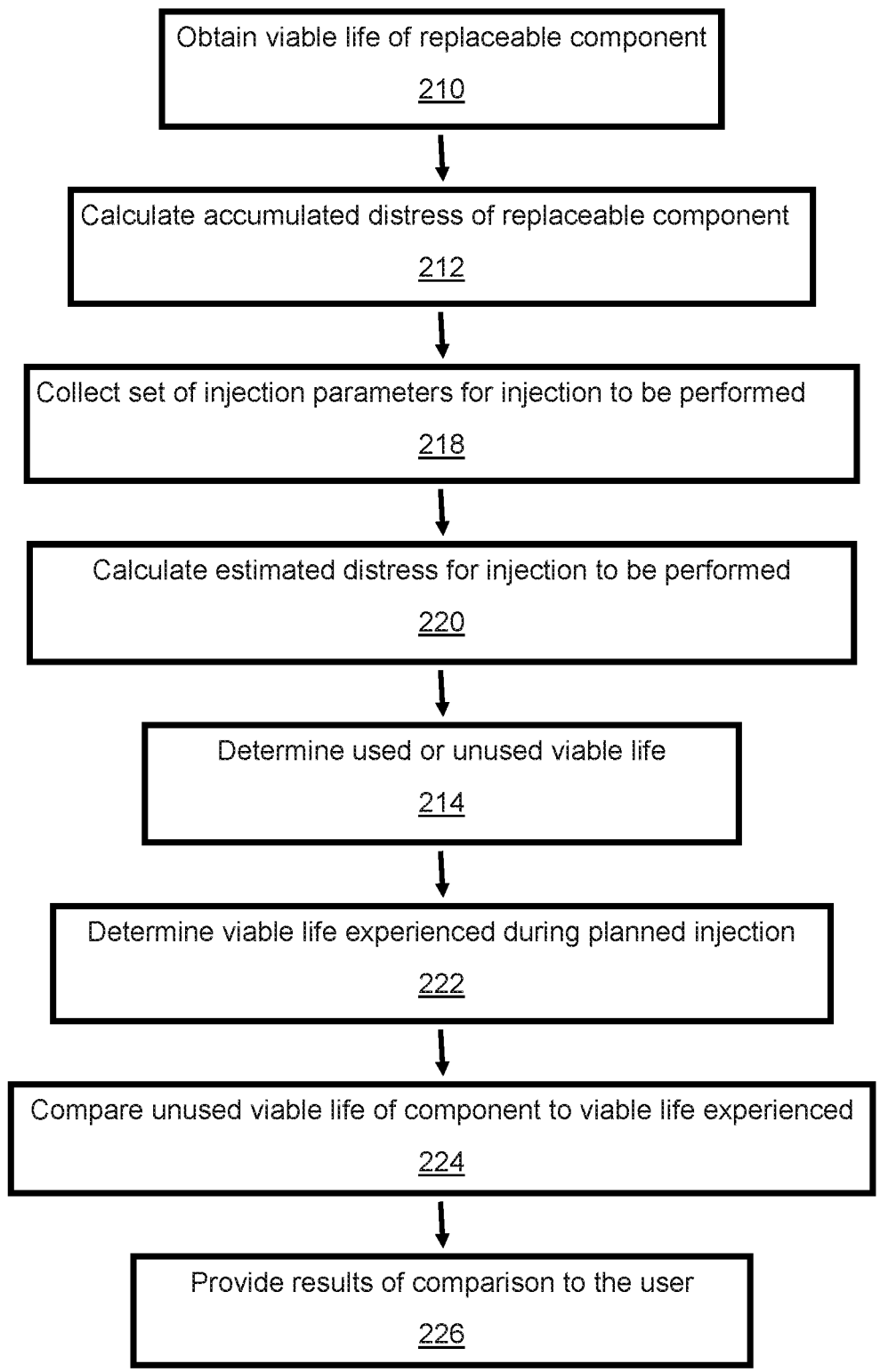
FIG. 9C is a flow chart illustrating steps for monitoring a fluid delivery system in which both previous and present uses of the replaceable component are considered.

With reference to FIG. 9C, a flow chart illustrating a method for monitoring status of a replaceable component is illustrated, which takes into account both accumulated distress and an estimated amount of additional distress provided by an injection to be performed. As in previously described examples, a viable life for the replaceable component of interest is provided to the controller 12, as shown at box 210. As shown at box 212, an accumulated amount of distress experienced by the replaceable component is calculated. For example, the calculated accumulated amount of distress can be based on sets of previously collected injection parameter data for injections performed using the injector and replaceable component of interest. At box 218, a present set of injection parameter data associated with a planned injection to be performed by the replaceable component is calculated and, in some cases, provided to the controller 12. At box 220, an estimated amount of distress that would be experienced by the replaceable component if the planned injection were performed is calculated. As shown at box 214, a used and/or an unused portion of the viable life of the replaceable component is calculated based on the accumulated amount of distress. At box 222, an estimated portion of the viable life of the replaceable component that would be experienced if the planned injection procedure were to be performed is calculated. At box 224, the unused portion of the viable life of the replaceable component is compared with the additional portion of the viable life that would be experienced by the replaceable component if the planned injection were performed to determine, for example, whether the replaceable component is suitable for the injection procedure to be performed. At box 226 results of the comparison are provided to the user in the manner discussed above in connection with FIG. 9B.

Figure 10:
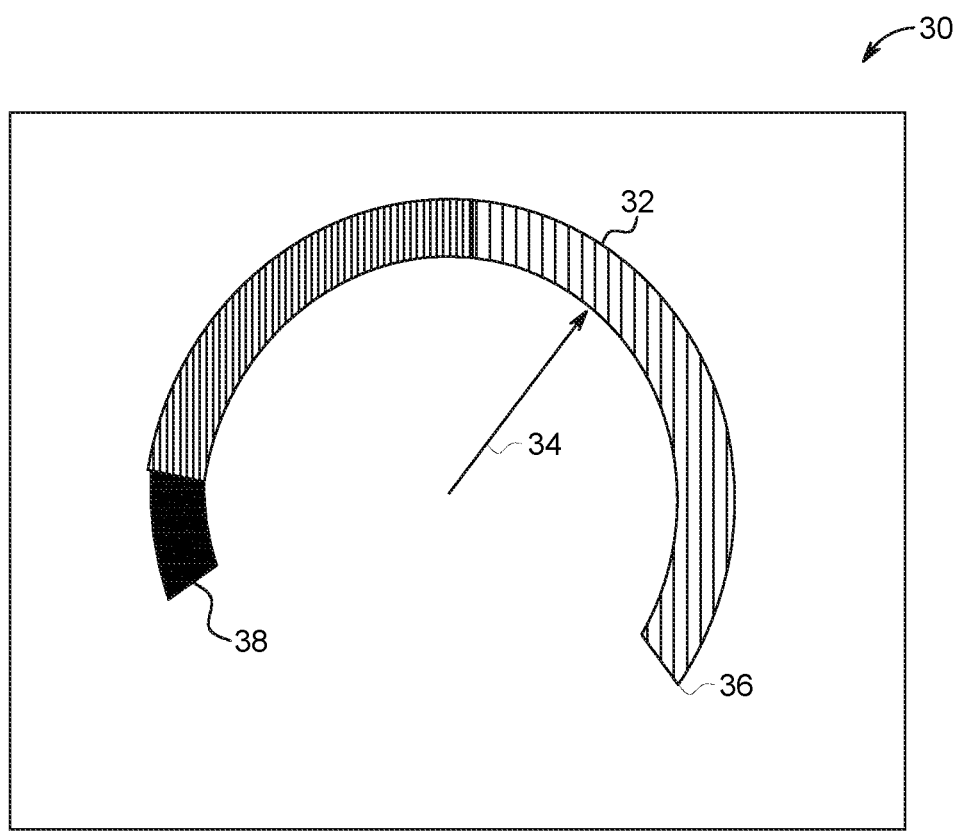
FIG. 10 is a feedback indicator for the fluid delivery system of FIG. 8.

With reference to FIG. 10, in one example, the visual display device 30 provides feedback about remaining or unused viable life in the form of a visual indicator 32 providing a graphical representation of remaining or unused viable life of the replaceable component. The visual indicator 32 can be in can be in the form of a gas gauge or dial, and can include an arm 34 that rotates between a full position 36 for a newly installed replaceable component and an empty position 38 when the replaceable component needs to be replaced. Alternatively, the visual indicator 32 could be a shape, such as a square or rectangle, having a specific fill amount. The fill amount can decrease following prolonged use to indicate that remaining or unused viable life of the replaceable component is decreasing. The fill amount can be color coded such that, as life expectancy decreases, the color of the fill amount changes from green to red. The operator can be instructed to remove and replace the component when the fill color of the visual indicator turns to red.

Having described the monitoring system 10 and a method of calculating the remaining or unused viable life of a replaceable component, additional embodiments of the monitoring system 10 will be discussed in detail. With reference again to FIG. 8, in some embodiments, the monitoring system 10 is configured to monitor multiple replaceable components simultaneously and to display feedback with the feedback device 14 about which replaceable component is closest to the end of its remaining or unused viable life. In this way, the component that is most in need of replacement (e.g., the weakest link component) can be identified and replaced. Replaceable components that still have unused viable life can continue to be used. For example, the controller 12 can be configured to track unused viable life for a number of the replaceable components simultaneously. In that case, the feedback device 14 can provide a separate remaining viable life indicator or numerical value for each replaceable component. The controller 12 can compare remaining viable life for each of these components and highlight the weakest link component. In addition, the feedback device 14 can display a warning or alert indicating which replaceable component is the weakest link and when it will need to be replaced.

In other embodiments, the monitoring system 10 can include an image sensor 40, such as a digital camera, infrared camera, or other known imaging device, for visually identifying or confirming that portions of the releasable component are breaking down. For example, the image sensor 40 can be configured to obtain images of portions of the injector 100 that are known to weaken following prolonged use. In some cases, the obtained images can show cracks or other indications that the component has been subjected to substantial stresses and is near the end of its viable life. In some embodiments, the cracks and other signs of distress can be identified automatically using image processing techniques, as are known in the art. For example, the image processing techniques can use color recognition techniques to identify cracks or other stress areas. Distance determination techniques can be used to determine the length of the cracks or size of the weakened areas. Similarly, the controller 12 can be configured to compare a recent image with one or more previously-obtained images to determine, for example, how fast cracks are expanding and other relevant information about accumulated distress to the replaceable components. The information obtained by image processing can be used in conjunction with other cumulative distress estimates to provide a more sophisticated indication of remaining or unused viable life for the replaceable injector component of interest. In particular, if substantial cracking is identified, the controller 12 can output an alert indicating that replacement is required, even if the algorithm otherwise indicates that the remaining or unused viable life of the component has been exhausted.

In view of the foregoing, it should be apparent to those skilled in the art that the monitoring system 10 of the present invention may be deployed with apparatuses other than the fluid injector system 100 described herein. For example, the monitoring system 10 may be applied to apparatuses such as infusion devices (e.g., a peristaltic pump, a syringe pump or an elastomeric pump) and centrifuge separators for use in, for example, separating whole blood into its various components (e.g., red blood cells, white blood cells and plasma) and DNA or RNA into fragments according to their size, and proteins according to their size and their charge.

Computing Unit or Device

As previously noted, calculations of remaining or unused viable life for the one or more replaceable injector components can be calculated by the controller 12. The controller 12 can be part of the electronic controller device that controls operation of the injector system 100. Alternatively, the controller 12 can be a remote computing device, such as a personal computer, which includes appropriate processing mechanisms and computer-readable media for storing and executing computer-readable instructions, such as programming instructions, code, and the like.

Figure 11:
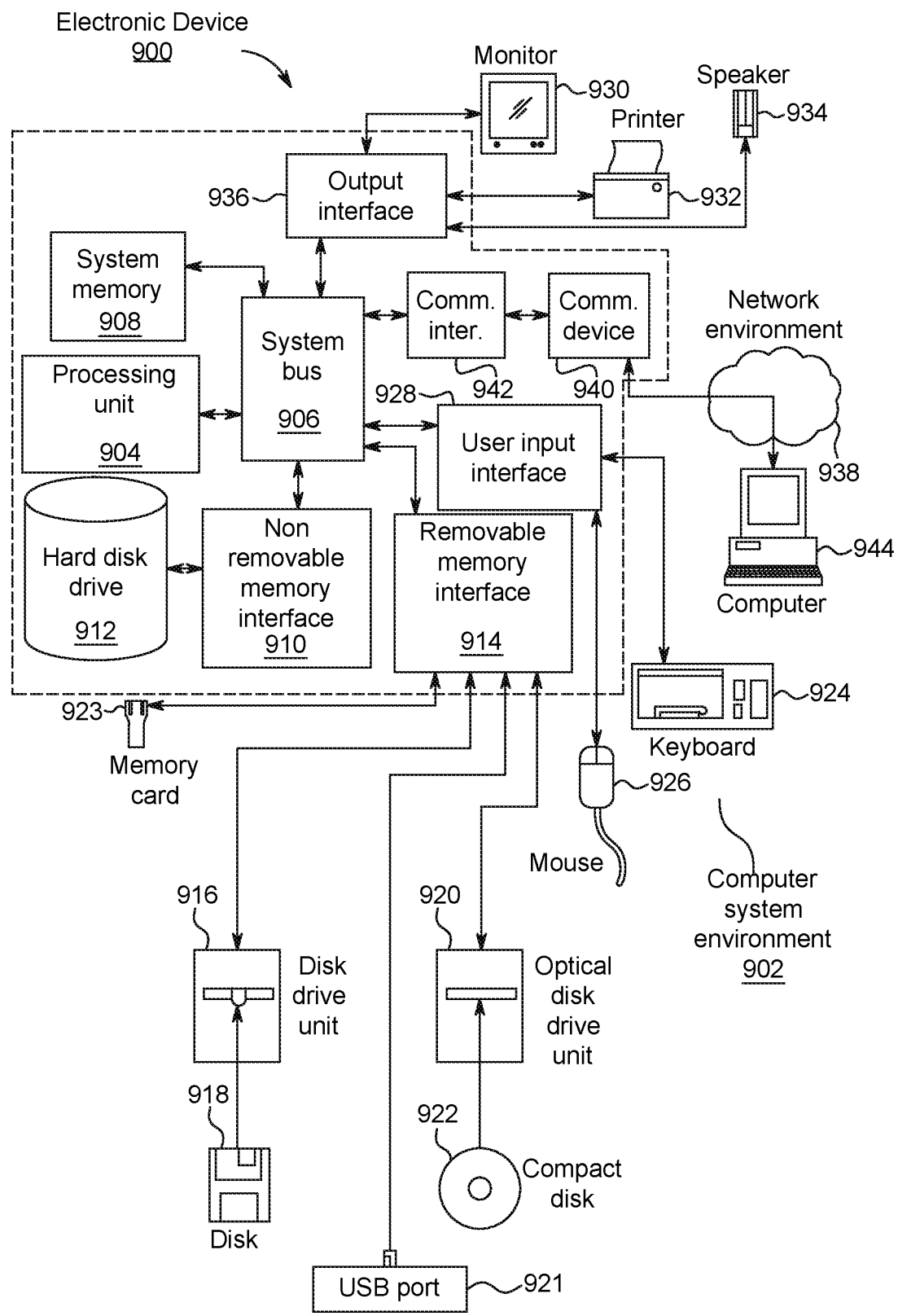
FIG. 11 is a schematic view of an electronic control device for use with the fluid delivery system of FIG. 8, in accordance with an aspect of the disclosure.

With reference to FIG. 11, an exemplary controller (referred to herein as an electronic device 900) is illustrated. The electronic device 900 can include a variety of discrete computer-readable media components. For example, this computer-readable media can include any media that can be accessed by the electronic device 900, such as volatile media, non-volatile media, removable media, non-removable media, etc. As a further example, this computer-readable media can include computer storage media, such as media implemented in any method or technology for storage of information, such as computer-readable instructions, data structures, program modules, or other data; random access memory (RAM), read only memory (ROM), electrically erasable programmable read only memory (EEPROM), flash memory, or other memory technology; CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic device 900. Further, this computer-readable media can include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic device 900 further includes a system memory 908 with computer storage media in the form of volatile and non-volatile memory, such as ROM and RAM. A basic input/output system (BIOS) with appropriate computer-based routines assists in transferring information between components within the electronic device 900 and is normally stored in ROM. The RAM portion of the system memory 908 typically contains data and program modules that are immediately accessible to or presently being operated on by the processing unit 904, e.g., an operating system, application programming interfaces, application programs, program modules, program data, and other instruction-based computer-readable codes.

With continued reference to FIG. 11, the electronic device 900 can also include other removable or non-removable, volatile or non-volatile computer storage media products. For example, the electronic device 900 can include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in the exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the electronic device 900 via the system bus 906. The drives and their associated computer storage media, discussed above and illustrated in FIG. 11, provide storage of operating systems, computer-readable instructions, application programs, data structures, program modules, program data, and other instruction-based, computer-readable code for the electronic device 900 (whether duplicative or not of this information and data in the system memory 908).

A user can enter commands, information, and data into the electronic device 900 through certain attachable or operable input devices via a user input interface 928. Of course, a variety of such input devices can be utilized, e.g., a microphone, a trackball, a joystick, a touchpad, a touch-screen, a scanner, etc., including any arrangement that facilitates the input of data, and information to the electronic device 900 from an outside source. As discussed, these and other input devices are often connected to the processing unit 904 through the user input interface 928 coupled to the system bus 906, but can be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic device 900 through an output interface 936 coupled to the system bus 906. It is envisioned that any such peripheral output devices be used to provide information and data to the user.

The electronic device 900 can operate in a network environment 938 through the use of a communications device 940, which is integral to the electronic device 900 or remote therefrom. This communications device 940 is operable by and in communication with the other components of the electronic device 900 through a communications interface 942. Using such an arrangement, the electronic device 900 can connect with or otherwise communicate with one or more remote computers, such as a remote computer 944, which can be a personal computer, a server, a router, a network personal computer, a peer device, or other common network nodes, and typically includes many or all of the components described above in connection with the electronic device 900. Using appropriate communication devices 940, e.g., a modem, a network interface or adapter, etc., the computer 944 can operate within and communicate through a local area network (LAN) and a wide area network (WAN), but can also include other networks such as a virtual private network (VPN), an office network, an enterprise network, an intranet, the Internet, etc.

As used herein, the electronic device 900 includes, or is operable to execute appropriate custom-designed or conventional software to perform and implement the processing steps of the method and system of the present disclosure, thereby forming a specialized and particular computing system. Accordingly, the presently-invented method and system can include one or more electronic control devices 900 or similar computing devices having a computer-readable storage medium capable of storing computer-readable program code or instructions that cause the processing unit 904 to execute, configure, or otherwise implement the methods, processes, and transformational data manipulations discussed hereinafter in connection with the present disclosure. Still further, the electronic device 900 can be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

It will be apparent to one skilled in the relevant arts that the system may utilize databases physically located on one or more computers which may or may not be the same as their respective servers. For example, programming software on computer 900 can control a database physically stored on a separate processor of the network or otherwise.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system capable of monitoring a replaceable component thereof, the system comprising:
   (a) a controller for controlling operation of the system;
   (b) programming instructions operably associated with the controller according to which the system is configured to
      (i) accept input of a viable life for a replaceable component of the system;
      (ii) calculate, using at least an algorithm comprising a model descriptive of material degradation of the replaceable component, an accumulated amount of distress experienced by the replaceable component based on use data associated with each previous use of the replaceable component by the system; and
      (iii) determine, based in part on the accumulated amount of distress, a used portion of the viable life that the replaceable component has experienced as a result of the use data and an unused portion of the viable life; and
   (c) a visual and/or audio feedback device configured to provide to an operator of the system an indication of at least one of the unused and used portions of the viable life of the replaceable component.

2. The system of claim 1, wherein:
   (a) the system is a fluid delivery system comprising a fluid injector; and
   (b) the use data associated with each previous use of the replaceable component by the system is injection parameter data associated with each injection procedure previously performed on one or more patients using the fluid injector;
   wherein the injection parameter data comprises one or more of an injection pressure, an injection time, and an injection temperature.

3. The system of claim 2, wherein the replaceable component being monitored by the fluid delivery system comprises at least one of a syringe, a tubing set, a valve, a fluid connector, a multi-patient fluid path set, a single-patient fluid path set and any combination thereof.

4. The system of claim 2, further comprising a sensing or timing device associated with a portion of the fluid injector and configured to collect the injection parameter data.

5. The system of claim 1, wherein the model is based on Miner's Rule or on an Inverse Power Law-Weibull Model.

6. The system of claim 1, wherein the use data comprises data collected from multiple portions of the system.

7. The system of claim 1, wherein the indication of at least one of the unused and used portions of the viable life of the replaceable component comprises displaying a visual representation of the used portion of the viable life relative to the viable life of the replaceable component.

8. The system of claim 1 wherein the viable life of the replaceable component is determined before the replaceable component is installed on the system.

9. A method of monitoring a status of a replaceable component of a fluid injector, the method comprising:
   (a) providing a viable life for the replaceable component;
   (b) calculating an accumulated amount of distress experienced by the replaceable component based on injection parameter data associated with each injection procedure previously performed therewith;
   (c) collecting a present set of injection parameter data associated with a planned injection procedure to be performed with the replaceable component;
   (d) calculating an estimated amount of additional distress that would be experienced by the replaceable component if the planned injection procedure were to be performed in accordance with the present set of injection parameter data;
   (e) determining, based in part on the accumulated amount of distress, a used portion of the viable life that the replaceable component has experienced as a result of the previously performed injection procedures and an unused portion of the viable life;
   (f) determining, based in part on the estimated amount of additional distress, an additional portion of the viable life that would be experienced by the replaceable component if the planned injection procedure were to be performed and, as a result, the replaceable component were to incur the estimated amount of additional distress;
   (g) comparing at least one of the unused and used portions of the viable life of the replaceable component to the additional portion of the viable life that would be experienced by the replaceable component if the planned injection procedure were to be performed; and
   (h) providing an indication of a result of the comparison to an operator of the fluid injector.

10. The method of claim 9, wherein the injection parameter data comprises one or more of an injection pressure, an injection time, and an injection temperature.

11. The method of claim 9, wherein the estimated and the accumulated amounts of distress are each calculated using at least an algorithm that employs a model descriptive of material degradation of the replaceable component.

12. The method of claim 11, wherein the model is based on Miner's Rule or on an Inverse Power Law-Weibull Model.

13. The method of claim 9, wherein the injection parameter data comprises data collected from multiple portions of the fluid injector.

14. The method of claim 9, wherein providing an indication of a result of the comparison comprises displaying a visual representation of the used portion of the viable life relative to the viable life of the replaceable component.

15. The method of claim 9 wherein the viable life of the replaceable component is determined before the replaceable component is installed on the fluid injector.

16. The method of claim 9, wherein the replaceable component comprises at least one of a syringe, a tubing set, a valve, a fluid connector, a multi-patient fluid path set, a single-patient fluid path set and any combination thereof.

17. The method of claim 9, wherein the accumulated amount of distress experienced by the replaceable component is initially zero when no injection procedure has been previously performed therewith and the planned injection procedure is intended as the first to be used therewith.

18. A disposable life indicator for measuring cumulative fluid pressure for a fluid injector, the disposable life indicator comprising:
- a fluid collecting portion in fluid communication with a fluid path set of a fluid injector; and
- a gauge configured to indicate to a user a used and/or an unused viable life for a replaceable component of the fluid injector based on a volume of fluid in the fluid collecting portion, the gauge comprising a piston moveably disposed within a bore of the gauge and configured to move therethrough as the volume of fluid in the fluid collecting portion increases.

19. The disposable life indicator of claim 18, further comprising a check valve disposed between the fluid path set of the fluid injector and the fluid collecting portion, the check valve being configured to permit fluid flow above a threshold pressure to access the fluid collecting portion.

20. The disposable life indicator of claim 19, wherein the check valve is a one-way check valve.

21. The disposable life indicator of claim 18, further comprising a flow restrictor positioned between the fluid path set and the fluid collecting portion for reducing velocity of a fluid flow entering the fluid collecting portion.

22. The disposable life indicator of claim 21, wherein the flow restrictor comprises a porous filter.

23. The disposable life indicator of claim 18, wherein the piston comprises a conspicuous tip configured to extend beyond an open distal end of the gauge in an end-of-use position.

24. The disposable life indicator of claim 18, wherein the gauge comprises a bourdon tube.

* * * * *

UNITED STATES PATENT AND TRADEMARK OFFICE
CERTIFICATE OF CORRECTION

PATENT NO. : 10,522,250 B2
APPLICATION NO. : 15/750878
DATED : December 31, 2019
INVENTOR(S) : Spohn et al.

Page 1 of 1

It is certified that error appears in the above-identified patent and that said Letters Patent is hereby corrected as shown below:

In the Specification
In Column 11, Line 61, delete "though" and insert -- through --, therefor.
In Column 13, Line 30, delete "publication)," and insert -- publication"), --, therefor.
In Column 15, Line 3, delete "injector 10" and insert -- injector 100 --, therefor.

Signed and Sealed this
Third Day of March, 2020

Andrei Iancu
*Director of the United States Patent and Trademark Office*